United States Patent [19]

Knutsson et al.

[11] Patent Number: 5,388,587
[45] Date of Patent: Feb. 14, 1995

[54] METHOD AND APPARATUS FOR MEASURING THE TRANSPORT TIME OF NERVE SIGNALS EXCITED IN DIFFERENT DERMATOMS OF A PATIENT

[75] Inventors: Evert Knutsson; Lennart Gransberg, both of Djursholm, Sweden

[73] Assignee: Dorsograf AB, Malmö, Sweden

[21] Appl. No.: 213,024

[22] Filed: Mar. 15, 1994

Related U.S. Application Data

[63] Continuation-in-part of Ser. No. 915,994, Aug. 4, 1992, Pat. No. 5,313,956.

[30] Foreign Application Priority Data

Dec. 4, 1990 [SE] Sweden ............................ 9003853

[51] Int. Cl.6 .............................................. A61B 5/05
[52] U.S. Cl. ...................................... 128/741; 128/732
[58] Field of Search ............... 128/732, 734, 741, 783, 128/795, 797, 905

[56] References Cited

U.S. PATENT DOCUMENTS

| | | | |
|---|---|---|---|
| 3,650,264 | 3/1972 | Janssen | 128/2.06 A |
| 4,064,870 | 12/1977 | Dumitrescu et al. | 128/2 N |
| 4,170,225 | 10/1979 | Criglar et al. | 128/733 |
| 4,570,640 | 2/1986 | Barsa | 128/741 |
| 4,794,934 | 1/1989 | Motoyama et al. | 128/734 |
| 4,807,643 | 2/1989 | Rosier | 128/741 |

Primary Examiner—Max Hindenburg
Attorney, Agent, or Firm—Fisher, Christen & Sabol

[57] ABSTRACT

Apparatus and method for diagnosing spinal disorders. Pairs, left and right, of symmetric dermatoms of a patient are individually excited by means of electrode pairs, and the "time of flight" is determined for impulses to arrive to the cortex. Due to noisy signals, it is necessary to register a substantial number of individual waveforms, control their integrity, exclude questionable waveforms and sum those not excluded. The invention makes possible the diagnosis of spinal disorders where prior art methods have failed although the patient is in pain.

4 Claims, 2 Drawing Sheets

METHOD AND APPARATUS FOR MEASURING THE TRANSPORT TIME OF NERVE SIGNALS EXCITED IN DIFFERENT DERMATOMS OF A PATIENT

RELATED APPLICATIONS

This application is a continuation-in-part of U.S. patent application, Ser. No. 915,994, filed Aug. 4, 1992 now U.S. Pat. No. 5,313,956, which is a U.S. national stage application of International Application No. PCT/SE91/00822, filed Dec. 3, 1991.

FIELD OF THE INVENTION

This invention regards measurement of transport times of nerve signals, in particular with the object of finding discrepancies which can be ascribed to deficiences at the spinal root level, and to localize the sites of such deficiences at the spinal level.

BACKGROUND OF THE INVENTION

It is well-known that cutaneous areas called dermatoms are distributed over the human body, which are connected to individual spinal segments. Excitation by electrical means of such cutaneous areas is known from U.S. Pat. No. 4,570,640 to Barsa, hereby included by reference into the present disclosure, and where the localizations of human dermatoms are explained and illustrated, including their respective conventional denominations. The purpose of electrical excitation of dermatoms in that disclosure is to determine the level and depth of nerve blocks, particularly for controlling anesthesia, the patient signalling by himself or through physiological measurement means the effect of excitations of varying strength. There is, however, no possibility disclosed for measuring the time of transport of nerve signals.

In the present case, however, the object is to determine the functionality of aspects of the nervous system, and in particular to diagnose conditions of spinal malfunction as evidenced from dermatom somatosensory evoked potentials (DSEP) and their time dependence.

In the prior art DSEP testing, an electrode pair is applied to a cutaneous area representative of a dermatom and electrical pulse signals are applied. The responses as received as cortex signals from the head are registered as related to the times of pulse application, summing a number of such signal waveforms in order to eliminate noise, the waveforms from individual pulses being heavily disturbed by noise. After registering about 150 waveforms, another dermatom is chosen, and a new set of waveforms is registered and summed. After registering results from a number of dermatoms, it is then necessary to repeat the operation, since it is established and wise practice not to trust an observation which does not have a guarantee of reproducibility. It is hardly possible to use a pulse repetition frequency in excess of about 3 per second, and each registering for a dermatom would therefore demand about one minute. A normal examination would need to operate on about 8 dermatoms (the human body having over 50 dermatoms), and the doubling of the procedure as presently needed would therefore, in the best of cases, take about 16 minutes. However, it is unlikely that a patient would be in the same state in relevant respects during such a time, the state of mind, variations in boredness, drowsiness, heaviness being likely to change the reactions. It should be kept in mind that the patient is in general not normally fit but likely to tire easily.

SUMMARY OF THE INVENTION

An object of the invention is to provide apparatus which will enable measurements of transport time to be carried out and which will also enable the transport time of nerve impulses from a plurality of dermatoms of the patient to the cortex to be mapped and compared within a short period of time with the patient normally awake, so as to enable the investigation to be carried out in polyclinic facilities. There is a great need for investigations such as these, particularly in the case of patients suffering from back trouble and back pains, where it is known at present that if the patient is put on the sick list and does not return to normal or rehabilitates within three months, the patient will become permanently unfit for work, in up to 90% of the cases involved. A quick diagnosis carried out in a polyclinic within a short space of time is able to save the majority of these people and to return them to a normal life, by treating the patients adequately in time. Further, there is particular value in being able to objectively assess back troubles, both for a patient to convince his doctor that his pain is real and no sham, and for an insurer to obtain proof of its reality.

A particular type of damage which should be assessed as well as possible is the so-called whiplash damage of the neck, occuring in traffic accidents, and where insurance benefits should be objectively assessed, and where at present great legal uncertainty often prevails due to lack of efficient diagnostic methods.

The monitoring of nerve signal speed is previously known and used for diagnosing certain types of nerve damage. For example, it is usual to apply electrical stimulating pulses over the posterial tibial nerve at the heel with the patient lying flat on his stomach, and to measure the arrival time at the brain cortex, by attaching two electrodes to the skin of the crown of the patient's head, wherewith in the case of a normal person a signal of the order of 0.5-3 $\mu V$ will occur between the electrodes after a time lapse of 39.5 $\pm 3.3$ ms from the time of administering the stimulating pulses. Although this signal contains a fair amount of noise, it is possible to obtain a summation signal from which the transport time can be determined with the aid of graphic methods or the like, by adding together a large number of signals.

Endeavours have also been made to obtain a more complete picture of the transport of the nerve signals, by positioning detectors along the spine, for instance so as to ascertain whether or not the function is influenced by defects in the spinal column. In this case, however, the disturbances which emanate from the muscles and the heart are much more troublesome. In order to eliminate these disturbances, incisive methods have been attempted, in which electrodes are inserted into the vertebral canal. Endeavours to measure the transport time of nerve signals have also been made with a combination of long measuring periods and patient relax periods, in which the patient is put to sleep or medicated. These investigations, however, cannot be carried out in polyclinics and are expensive, time consuming and somewhat unpleasant for the patient.

A particular problem in measurement of dermatomal somatosensory evoked potentials (DSEP) is that a patient is not a reproducible thing, i.e. the result in measured time will be subject to irregular variations. In the prior art, it has therefore been common practice to reproduce the respective measurements for obtaining the "same" result twice at least. Lack of reproducibility is indeed a problem, and it is an object of the invention to substantially eliminate this factor.

The most important problem solved by means of the present invention pertains to the signal to noise ratio in its widest meaning. Firstly, the signals are very small and are therefore subjected to normal noise. Secondly, artifacts exist, i.e. disturbances in the form of muscle impulses for instance, EMG, and impulses deriving from cardiac activity, ECG.

These problems are far less troublesome when the signals are detected with the aid of electrodes placed on the crown of the patient's head, since only smaller artifacts are caused by the spontaneous activity of the cerebral cortex, EG, and to some extent by eye movements.

Another difficulty is encountered when wishing to make a comparitive investigation between the left and the right side of a patient. In conventional methods, first the one side is investigated and then the other. The result is often unreliable, because of variations in excitability within the central nervous system.

Consequently, in accordance with the invention, at least two sets of stimulating electrodes and generally a plurality thereof, are attached to respective dermatoms, and activated alternately, the storage and processing of the resultant signals being effected in separate memory stores. It is suitable to activate a right side dermatom each alternate time and to activate a corresponding left side dermatom at times therebetween. In general, it is practical to select a plurality of symmetrical pairs of dermatoms, guided by the patient's symptoms as to ailment. The dermatoms may then be scanned by repetitive stimulating signals in a predetermined order. The results will then be automatically compensated for drift in the patient's nervous condition, which otherwise creates great difficulties with presently utilized practice.

BRIEF DESCRIPTION OF THE FIGURES

The invention will now be described in more detail on the basis of a non-limiting exemplifying embodiment thereof.

DESCRIPTION OF THE PREFERRED EMBODIMENTS

Figure 1:
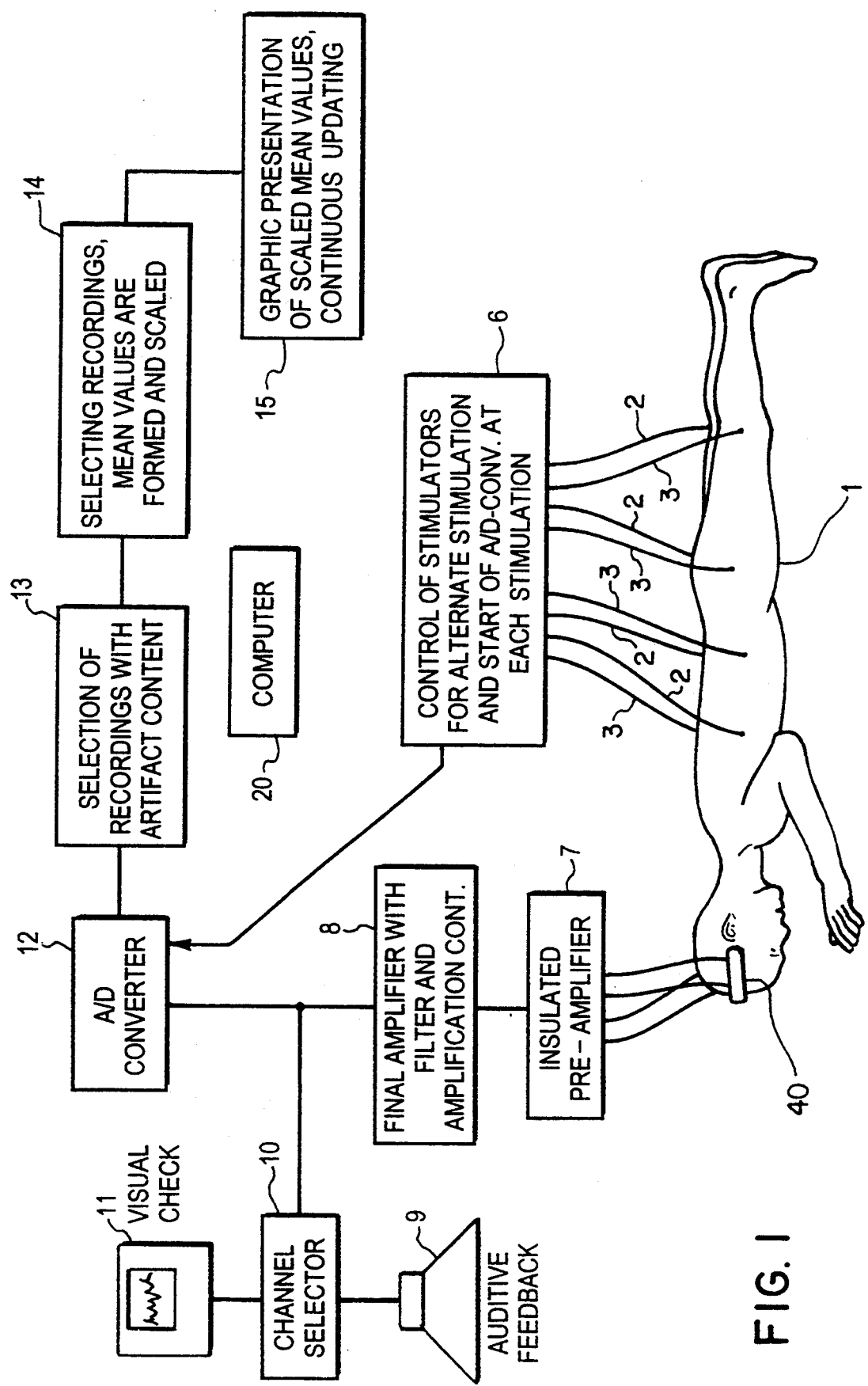
FIG. 1 illustrates schematically an inventive apparatus connected to a patient.

FIG. 1 is a block schematic which illustrates the principal construction of the exemplifying inventive apparatus. Some of the blocks shown denote functions which are carried out in a computer 20, and consequently the Figure shall be read partially as a flowsheet.

A patient 1 lies flat on his stomach on a bed or like support surface, as comfortably as possible. Pairs of electrodes 2, 3 are attached conductively to the skin on a number of the patient's dermatoms, as schematically shown, no indications of actual dermatoms being shown in this figure. Similar electrodes are attached at 40 on the crown of the patient's head. In order to catch signals stemming from various dermatoms, it is preferred to arrange electrodes on the head over the sensory cortex excited from the various dermatoms.

Connected to the electrodes 2, 3 are electric stimulators 6, which may be of a conventional kind capable of delivering voltage pulses that can be adjusted between 100–200 V with durations of 0.1–0.5 ms, or current pulses of 0–40 mA of the same durations. The stimulators are controlled by the computer 20 so as to deliver stimulation pulses at a pulse rate of 2–5 Hz. There are produced in this way nerve signals which pass up via respective dermatoms into the nerve paths of the spinal cord and up to the cortex. The signals are finally caught from the cortex through the electrodes 40. The electrodes 40 are connected, via earth screened conductor pairs, to an insulated preamplifier 7 and a following final amplifier 8 with filters and variable amplification which is either adjusted manually or adjusted to suitable amplification levels by means of the computer, so as to obtain a range suitable for receipt by a multiplex-operating A/D-converter. This converter may be a conventional 12-bit converter capable of detecting in time-multiplex all of the amplified signals, each having a sampling frequency of 2 kHz. Sampling begins at each stimulator pulse and has a duration of 100 ms, so as to obtain for each "simultaneously" measured electrode a time-series of 200 values per shot.

FIG. 1 also illustrates schematically the manner in which one of the signals arriving from the final amplifiers can be selected with the aid of an adjustable channel selector 10. This selected signal can be observed with the aid of a conventional oscilloscope 11 and passed to a loudspeaker 9, so that the patient is able to hear his own signals. Since muscle activations result in disturbances which may disturb the nerve signals, it is possible, by auditive feedback, to induce a concentrated patient to reduce this muscle activity, despite the fact that this muscle activity is not fully conscious or subjectively will-controlled. This is a surprisingly effective mechanism which in an advantageous embodiment contributes greatly to the good effect achieved by the present invention.

The output signals from the final amplifier 8 are passed to the A/D-converter where said signals are sampled. The sampled signals are selected with the aid of the computer 20, here drawn in the form of a box 13 and the mean values of the signals are formed in the box 14, and the results are successively displayed graphically on a screen 15. The boxes 6, 12, 13, 14 and 15 actually denote operations carried out by the computer, and consequently FIG. 1 should be seen partially as a flowsheet explaining the connection between the electrodes affixed to the patient and the measuring processes carried out.

The recorded measurements are processed in the following manner, in accordance with a computer program:

(1) Those series which present at least one value for which the A/D-converter has become saturated ("all ones") are rejected.

(2) In order to obtain a first characteristic quality factor, or merit factor, there is calculated for respective series the sum of the absolute values of the differences between pairs of adjacent values, e.g. values having a mutual order difference of 4:

$$A = \Sigma \; |X_i - X_{i-4}| \quad 4 \leq i \leq 200$$

(3) In order to obtain a second characteristic quality factor, there is calculated in the same way the sum of the differences between pairs which lie at a greater distance apart, e.g. 40 units:

$$B = \Sigma \; |X_i - X_{i-40}| \quad 40 \leq i \leq 200$$

(4) In order to obtain a third characteristic quality factor, there is first calculated the maximum difference between two values separated by 4 samplings:

$$C = \max |X_i - X_{i-4}| \quad 4 \leq i \leq 200$$

(5) A fourth characteristic quality factor is used in that for each activated dermatom, 25 numerical sequencies for the same dermatom, each representing a stimulating electrical signal, are summed, and the amalgamated result is compared by autocorrelation with the next amalgamated 25 numerical sequencies for the same dermatom. Series from the same dermatom which do not give a satisfactory likeness are discarded. In a first stage, 100 such sequencies are recorded per dermatom examined, for instance for each measuring signal which has not been rejected in accordance with (1) above. Thus, 100 value triads are obtained for these series. These can be seen as a shower of points in three-dimensional space laid in a space quadrant. These value triads are used to calculate a final criterion consisting of three numbers, such that, e.g., 25% of the 100 value triads satisfy this final criterion. For example, it is possible to calculate the mean value of each quality factor and to calculate the percentage thereof required for said rejection to be set to 25%.

The actual measuring series begins when the first 100 series have been recorded and the triads stored. For each new measurement series of 200 values, the value triads are calculated and compared with the final criterion. If this criterion is satisfied by all three values, each of the 200 values is stored in its respective memory. Thus, successive accepted values are added together and ultimately there are obtained 200 mean values which when plotted form a curve which becomes progressively better and free from noise.

At the same time, the new value triad is recorded, while the first recorded value triad is discarded and a new final criterion is calculated. Thus, the final criterion is calculated in accordance with what can be called an iterative process which is adapted to prevailing conditions.

FIG. 1 illustrates these operations schematically in the box 13, where selection and triad storage takes place, whereas the accepted series are stored during successive formation of mean values in the box 14. The mean values of the curves can then be viewed successively on a screen in the box 15, and when the curves are considered satisfactory, the measuring process can be interrupted and the result printed out. Thus, curves are obtained from several dermatoms along the path travelled by the nerve signal to the cortex.

The following procedure is taken for eliminating noise and artifacts:
a) Slow variations are already eliminated in the final amplifier 8, through a high pass filter, e.g. a RC-filter having a limit frequency of 0.5 Hz.
b) When the A/D-converter 12 bottoms, the whole of the series being recorded at that time is rejected.
c) Series having an excessively high frequency content are eliminated by the quality factor A.
d) Series having excessive slow variations are eliminated by the quality factor B.
e) Series with a large number of pronounced variations are eliminated by the quality factor C.

These rejection criteria can be varied in many ways. What is essential is that each individual value array is subjected to variation criteria and either accepted or rejected as a whole, whereas the accepted values are summated point by point to obtain the mean values.

With regard to the aforesaid adaptive, auditive feedback, which may sometimes be used to improve the results, this is effected by passing one of the signals most subjected to muscle disturbances, thus a signal obtained from a pair of the electrodes 40, suitably amplified, to a loudspeaker 9, through a channel selector 10. The same signal can also be sent to an oscilloscope 11, for visual monitoring purposes. In certain cases, instead of using a loudspeaker, it may be more appropriate to use headphones worn by the patient. In the case of deaf people, it is suitable to position the oscilloscope 11 so that it can be seen by the patient. It has been found that, in general, the patient is able to lie still over at least prolonged periods, so as to practically eliminate muscle disturbances as a disturbance source, especially in combination with the aforesaid disturbance elimination.

EXAMPLE

The following is an example of the results when the invention was applied to a patient. The patient, age 25, 190 cm tall, had been complaining for about 18 months about pain in the lower part of the back, and had gone through a substantial amount of examination, such as neurologic-clinic, MRT (a tomographic method), EMG. No fault was found, and suspicion had arisen that the case was of a substantially psychic nature. The present invention was then tried.

Figure 2:
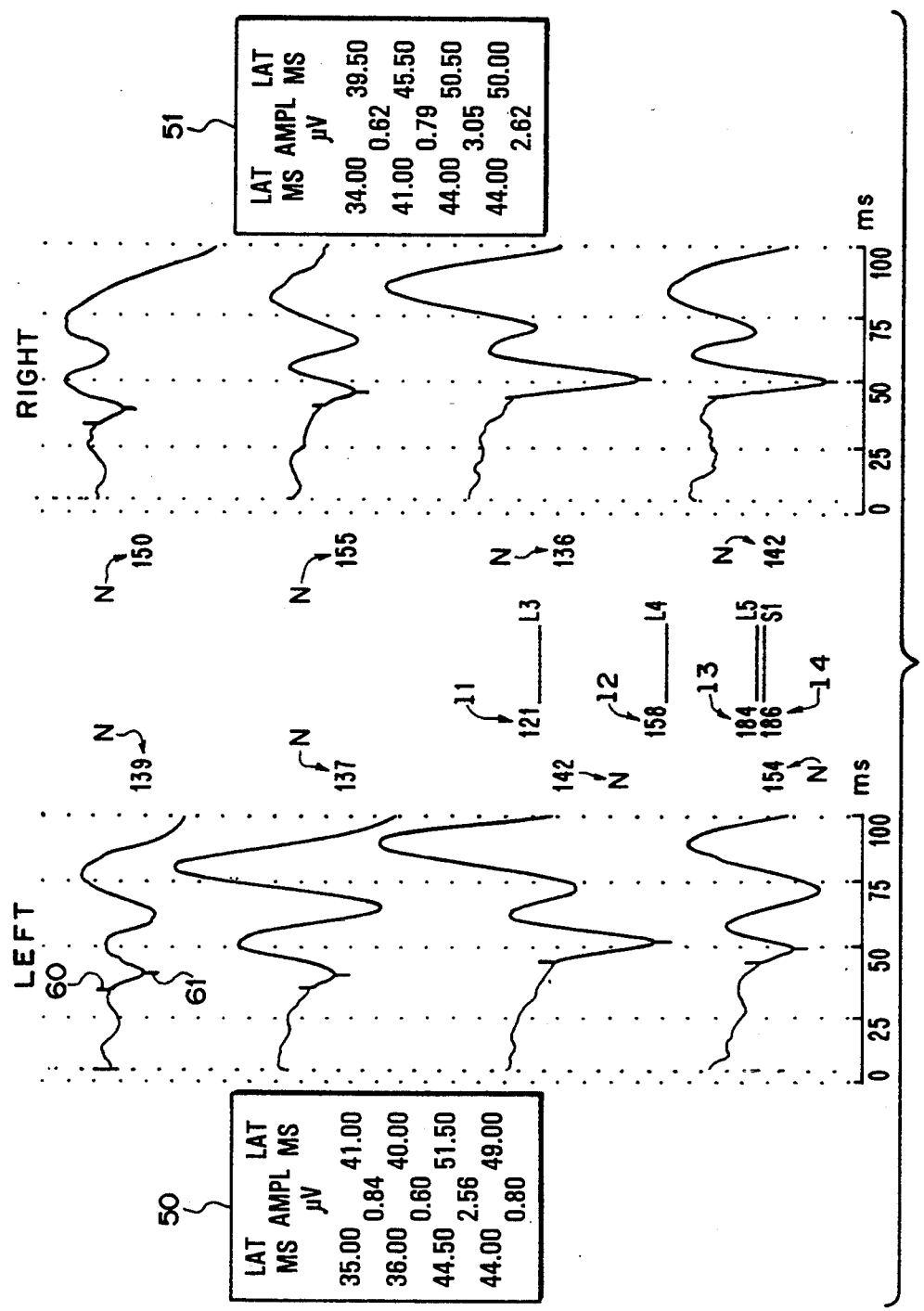
FIG. 2 demonstrates the results, as shown on a monitor, for a measurement series made on a patient suffering from back pain.

Due to the location of the symptoms as described by the patient, the four pairs (left and right) of dermatoms S1, L5, L4 and L3 were chosen for the test, and electrode pairs were applied on those dermatoms. The results are shown in FIG. 2 as presented on a display. Four pairs of curves, left and right, are apparent, each a combination of a number N of individual curves. Numerical latency values are shown in boxes 50 (left) and 51 (right). Apparently, the curves have varying patterns, and in order to obtain characteristic values, the first substantial drop point as 60 is registered for each curve, together with the first minimum 61, which is also registered, and which is determinable with better precision and therefore taken as the "best" point for determining the transport time or latitude. Both values are given in boxes 50, 51, together with the amplitude in arbitrary units, calculated between the two registered points of the respective curves.

In the diagram of FIG. 2 are further registered calculated approximate transport lengths 11, 12, 13, 14 for nerve transport lengths for the respective dermatoms L3, L4, L5, S1.

An analysis of the results was made between left and right dermatoms A variation between left and dermatoms of the same denomination of less than 2.5 ms is not considered abnormal. In this case, a difference larger than this was observed only for dermatoms L4, namely, 5,5 ms, the right dermatom giving a slower reaction. Thus, it could be inferred that something was the matter with the L4 root. Further examination could exclude a disc slip, and it was found that the corresponding vertebra had an excessive movability, due to muscular weakness. The patient is now given physiotherapy directed toward strengthening of relevant muscles, and the progressive rehabilitation is now sucessfully under way.

The actual examination giving the result as shown in FIG. 2 demanded between 7 and 8 minutes, plus the time for finding the dermatoms and positioning the electrodes.

The Example shows well the utility of the invention for diagnosing back pain symptoms which are notoriously difficult to diagnose. According to the invention, it is possible in general to discover sham symptoms and exclude fraud on insurance companies. Equally important is that it gives increased possibilities of exact diagnosis and, if possible, adequate treatment, of back pains even in patients where no objective symptoms could be found with earlier methods.

We claim:

1. An apparatus for measuring the transport time of nerve signals of a patient, said apparatus comprising
   (a) a plurality of stimulating electrodes capable of transmitting electrical signals to a plurality of selected skin portions of a patient,
   (b) a plurality of detecting electrode pairs adapted for attachment to the patient's head skin,
   (c) amplifying means connected to said detecting electrode pairs and capable of amplifying the electrical signals detected by said detecting electrode pairs,
   (d) an A/D-converter capable of receiving the amplified electrical signals generated by said amplifying means,
   (e) a computer capable of processing the amplified electrical signals received by said A/D-converter and storing said signals as numerical sequences at specific time points related to time points of stimulation by each of said stimulating electrodes,
   (f) means for exciting each of said stimulating electrodes of said plurality in a predetermined order for obtaining pluralities of said numerical sequences,
   (g) means for excluding select numerical sequences,
   (h) means for making sums of numbers in numerical sequences not excluded in step (f) and excited by each of said pairs of exciting electrodes, for obtaining numerical sum sequences which are time related to respective transmitted electrical signals for each of said exciting electrodes, and
   (i) means for mutually comparing numerical sum sequences obtained by stimulating different stimulating electrodes for determining differences in transport times for nerve signals excited at different skin locations on the patient.

2. The apparatus according to claim 1, comprising means for signaling the output signals from said amplifying means to the patient's consciousness.

3. A method of measuring the transport time of nerve impulses as the nerve impulses travel from a selected skin portion of a patient to the cortex of said patient, said method comprising:
   (a) attaching a plurality of stimulating electrodes to skin portions of selected dermatoms of the patient and applying stimulating electrical signals to said plurality in a predetermined interdigitating order,
   (b) attaching a plurality of detecting electrode-pairs to the head skin of said patient,
   (c) amplifying the electrical signals detected by said electrode-pairs,
   (d) transmitting the amplified electrical signals of
   (c) to an A/D-converter,
   (e) processing and storing the amplified electrical signals received by said A/D-converter in a computer as numerical sequences at specific time points related to time points of stimulation for each of said stimulating electrodes,
   (f) excluding select numerical sequences,
   (g) summating numbers in remaining numerical sequences into respective sum sequences appertaining to each separate of said stimulating electrodes, and
   (h) mutually comparing said sum sequences appertaining to different selected dermatoms for determining differences in transport times for nerve signals.

4. The method of claim 3, wherein at least one pair of symmetric dermatoms of the patient is provided with stimulating electrodes, for determining degree of symmetry in nerve signal transport time between opposite sides of the patient's body.

* * * * *